United States Patent [19]

Welker

[11] Patent Number: 4,631,967
[45] Date of Patent: Dec. 30, 1986

[54] AUTOMATIC INSERTION DEVICE

[75] Inventor: Robert H. Welker, Sugar Land, Tex.

[73] Assignee: Welker Engineering Company, Sugar Land, Tex.

[21] Appl. No.: 735,052

[22] Filed: May 17, 1985

[51] Int. Cl.⁴ .............................................. G01N 1/10
[52] U.S. Cl. ............................... 73/861.25; 73/861.66; 73/866.83; 73/863.82; 73/863.83; 73/863.86; 73/866.5
[58] Field of Search ........... 73/432 R, 863.81, 863.82, 73/863.83, 863.84, 863.85, 863.86, 861.25, 861.66, 861.83, 866.5; 138/94, 94.3, 94.5; 374/209

[56] References Cited

U.S. PATENT DOCUMENTS 3,007,340 11/1961 Kraftson ............................ 73/432 R
4,479,393 10/1984 Shores .......................... 73/863.86 X Primary Examiner—Jerry W. Myracle
Attorney, Agent, or Firm—Gunn, Lee & Jackson

[57] ABSTRACT

The automatic insertion device will insert or withdraw a piston rod into a pressurized fluid pipeline. In one embodiment, the piston rod will allow intrumentation on the exterior of the pipeline to directly sense the pressure of the fluid inside of the pipeline. In an alternate embodiment, the piston rod may be used to remove liquids from the pressurized pipeline. In the preferred embodiment, a cap is put on the end of the piston rod to isolate it from the pressure inside of the pipeline. The automatic insertion device can then be equipped with a turbine meter, a temperature sensor, or doppler measuring equipment. In another embodiment, a pitot probe can be placed on the end of the pipeline for measurement of differential pressure which, with additional instrumentation, can be used to measure flow through the pipeline. In another embodiment, the automatic insertion device can be combined with a pump to remove samples of the fluid within the pipeline.

32 Claims, 10 Drawing Figures

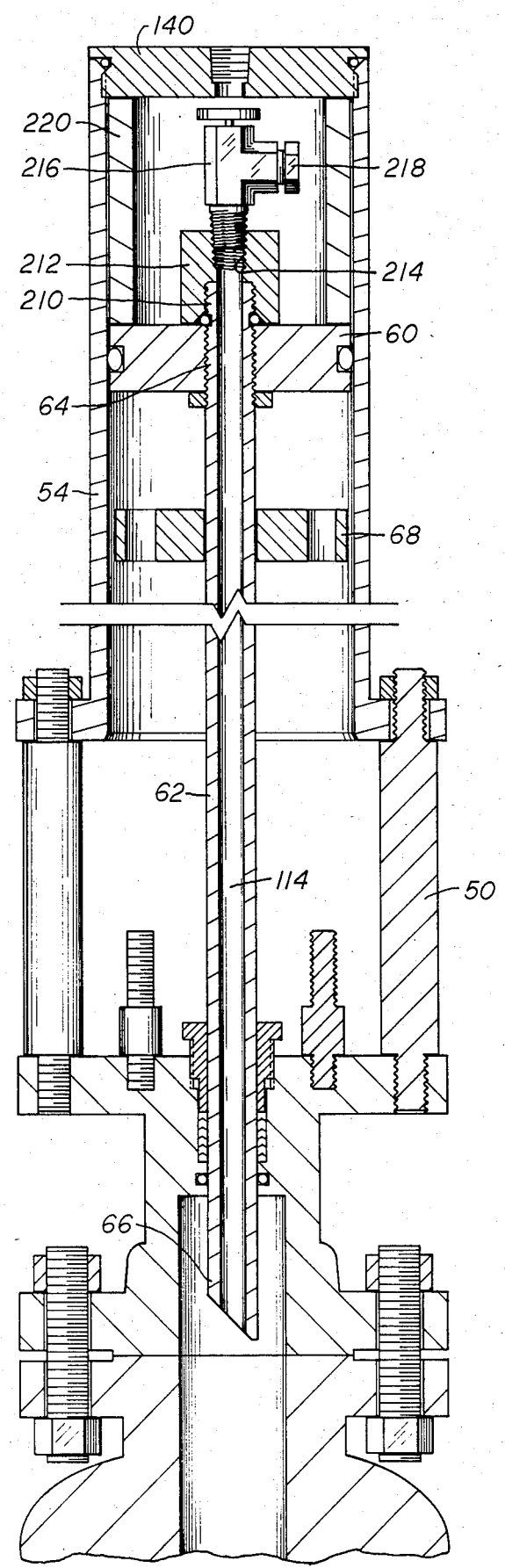

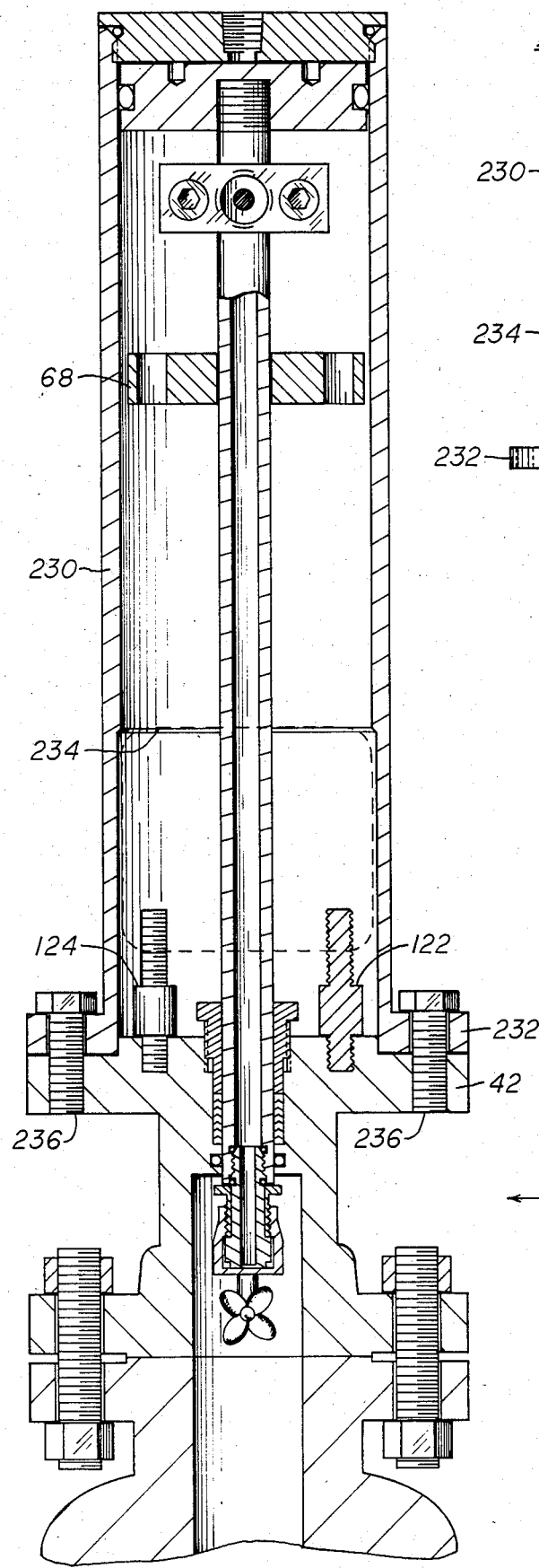
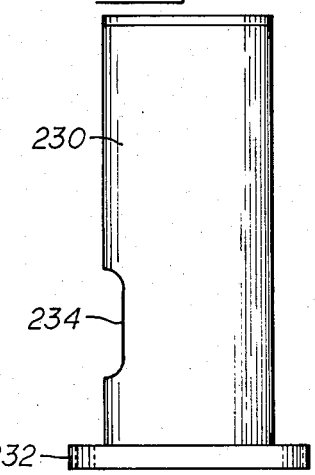

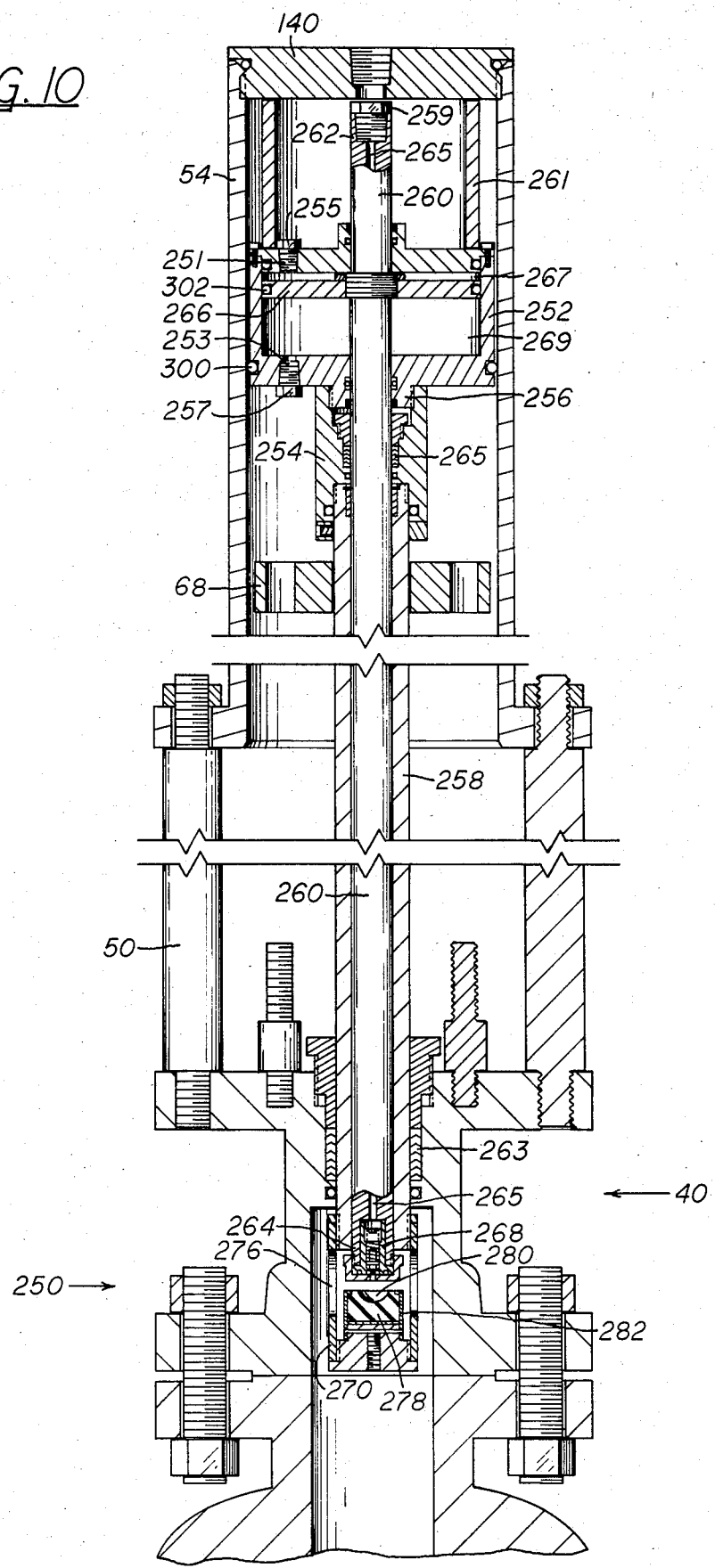

AUTOMATIC INSERTION DEVICE

BACKGROUND OF THE DISCLOSURE

1. Field of the Invention

This automatic insertion device may be used to sense the pressure inside of a fluid pipeline or to remove liquids therefrom. The preferred embodiment may be used to insert various types of sensors or measuring devices into a pipeline, e.g. a turbine meter, a temperature sensor, a pitot probe, or a doppler flow measuring device. Another embodiment may be used for insertion of a pumping device sometimes referred to as a sampler.

2. Description of the Prior Art

U.S. Pat. No. 4,177,676 which issued on Dec. 11, 1979, discloses a "Sensor Positioning Apparatus" which was invented by Robert H. Welker. The apparatus disclosed in the '676 patent uses a double acting cylinder and was designed to be permanently installed on a pipeline. Welker Engineering Company has sold various devices which embody the concepts disclosed in the '676 patent; however, the overall length of the apparatus in contrast with overhead clearance sometimes limits its use.

After a pipeline has been constructed, it will sometimes be necessary to install a sensor or other device at some remote location. Because the pipeline is typically located underground, a pit must be dug in order to gain access to the pipeline. The typical pit will be fitted with doors which close over the pit protecting it from rain and snow. The doors also prevent cattle, people, snakes and other creatures from falling into the pit. In most situations, the apparatus described in the '676 patent, when mounted on the pipeline in a pit, has prevented closure of the pit doors. Because of the double acting cylinder, it was impossible to shorten the overall height of the apparatus. In these situations, the pits fill with water and/or snow which makes maintenance difficult, if not impossible.

U.S. Pat. No. 4,387,592, which issued on June 14, 1983, discloses a "Probe Insertion Apparatus" which was invented by Robert H. Welker. Welker Engineering Company has sold various devices which embody the concepts disclosed in the '592 patent. The apparatus disclosed in the '592 patent relies upon a single acting cylinder connected by means of a yoke to an elongated probe body. The apparatus can be disassembled after the probe body has been inserted into a pressurized pipeline; however, the configuration is also limited by clearance. If the single acting cylinder is not removed, the apparatus shown in the '592 patent has the same height disadvantages as the apparatus disclosed in the '676 patent.

U.S. Pat. No. 4,346,611 which issued on Aug. 31, 1982, discloses an "Insertion Regulator for Pressurized Pipelines" which was invented by Robert H. Welker. The '611 patent discloses an apparatus to be permanently connected to a pipeline for inserting and removing a regulator therein.

All of the aforementioned inventions disclose an apparatus which is rather lengthy and therefore limited in use. In pit applications, the height of these devices frequently prevents closure of the pit doors, allowing the pit to fill with rainwater and/or snow. These space limitations cannot be overcome because the depth of the subsurface pipeline is not subject to alteration. Leaving pit doors open is not wise because reptiles and other noxious creatures frequently find their way into the pits if the doors are not securely closed which makes maintanance and service of these devices most unpleasant.

In aboveground installations, the aforementioned devices are typically enclosed in a sheet metal building or shed. In some installations, it will be necessary to cut a hole in the top or side of the shed to accommodate these devices or build a larger shed at increased cost. In other aboveground installations, there may be a series of parallel pipelines spaced three to four feet apart. If a horizontal installation is required in a parallel piping situation, many of the aforementioned devices cannot be used because of their overall length. Again, the spacing of the piping is not subject to easy or economical alteration.

The present invention is approximately 40% shorter in overall length than the aforementioned prior art devices when measured before insertion of the turbine or other sensor into the pipeline. This reduction in overall length allows the placement of insertion devices in many parallel piping situations which were not heretofore accessible by prior art devices. For example, a prior art device for insertion in a 24 inch pipeline would be approximately 82 inches in overall length; the present invention for insertion in a 24 inch pipeline would typically be 47 inches in overall length prior to insertion and removal of the cylinder.

In some situations, a doppler measuring device will be applied to a pipeline for measuring flow. Some doppler flow measuring devices require a horizontal installation with a transmitter on one side of the pipeline and a receiver on the opposite side of the pipeline. In some applications, both the transmitter and receiver are mounted on one insertion device; in other applications, the transmitter and receiver can utilize separate automatic insertion devices. If it is necessary to dig a pit to accommodate subsurface installation of two automatic insertion devices on a horizontal mode, any reduction in overall length of the automatic insertion device is an advantage because it reduces the size of the pit.

A group of other patents owned by Northern Natural Gas Company and/or Internorth, Inc. disclose various siphon devices including U.S. Pat. Nos. 4,155,376, issued on May 22, 1979; 4,282,894, issued on Aug. 11, 1981; and 3,345,616 issued on Aug. 24, 1982. All of these siphon patents disclose an apparatus which is long, ungainly and cumbersome.

The present invention discloses a compact apparatus which overcomes many of the disadvantages and problems associated with prior art devices.

The current invention, with slight modification, can be used for a multitude of applications, making it an extremely attractive product from the manufacturer's point of view. The current invention can be used as a pressure sensor or to withdraw fluids from a pipeline; in one version, it can be used for the insertion of a temperature sensor, a pitot probe, a turbine meter, or a doppler measuring device. An alternate embodiment allows insertion and withdrawal of a pump or sampling device into and from a pipeline.

High pressure pumps have been disclosed in U.S. Pat. No. 3,945,770 by Robert H. Welker. Improvements in this apparatus are further disclosed in U.S. Pat. No. 4,403,518 and pending application Ser. No. 06/456,328 and Ser. No. 06/222,362, also by Robert H. Welker. These pumps have been used to place odorants and hydrate inhibitors in natural gas pipelines; they have also been used in cryogenic service to pump liquid carbon dioxide. They have been used in other applications to pump various fluids such as water. These pumps have been integrated with sample vessels as disclosed in patent application Ser. No. 06/654,937 by Brian H. Welker. In U.S. Pat. No. 4,440,032, a sampler incorporating a purge system is disclosed. Vacuum breakers for use in high pressure pumps are disclosed in U.S. Pat. No. 4,470,773.

SUMMARY OF THE INVENTION

This automatic insertion device may be used as a pressure sensor to connect instrumentation with a pressurized fluid pipeline or in another embodiment may be used to withdraw liquids from a pipeline.

In an alternative embodiment, the automatic insertion device can be equipped with a temperature sensor for measuring the temperature inside of a pressurized fluid pipeline. In another embodiment, a pitot probe can be inserted into the pipeline to measure differential pressures. Instrumentation can then calculate the volume of flow through the pipeline, given the differential pressure. In another embodiment, the automatic insertion device can be equipped with a turbine meter which is another device used for measuring flow through the pipeline. In another embodiment, the automatic insertion device can be equipped with a doppler measuring instrument which is yet another means of measuring flow through a pipeline.

Another embodiment allows insertion and withdrawal of a pump or sampling device into and from a pipeline. The pump transfers an aliquot portion of fluid from the pipeline to a sample container. The sample container is typically taken to a laboratory for analysis. In natural gas applications, the BTU content of the sample is of critical importance.

BRIEF DESCRIPTION OF THE DRAWINGS

So that the manner in which the above recited features, advantages and objects of the present invention are attained and can be understood in detail, a more particular description of the invention briefly summarized above, may be had by reference to the embodiments thereof which are illustrated in the appended drawings.

It is to be noted, however, that the appended drawings illustrate only typical embodiments of the invention and are therefore not to be considered limiting of its scope, for the invention may admit to other equally effective embodiments.

FIG. 7 is a section view of an alternate embodiment of the automatic insertion device capable of sensing pressure or removing fluids from the pipeline.

FIG. 8 is a perspective view of an alternate embodiment of the cylinder with a window therein.

FIG. 9 is a section view of an alternate embodiment of the automatic insertion device with a window shown in phantom in the cylinder.

FIG. 10 is a section view of an automatic insertion device with a pump or sampler attached thereto.

DESCRIPTION OF THE PREFERRED EMBODIMENT

Figure 1:
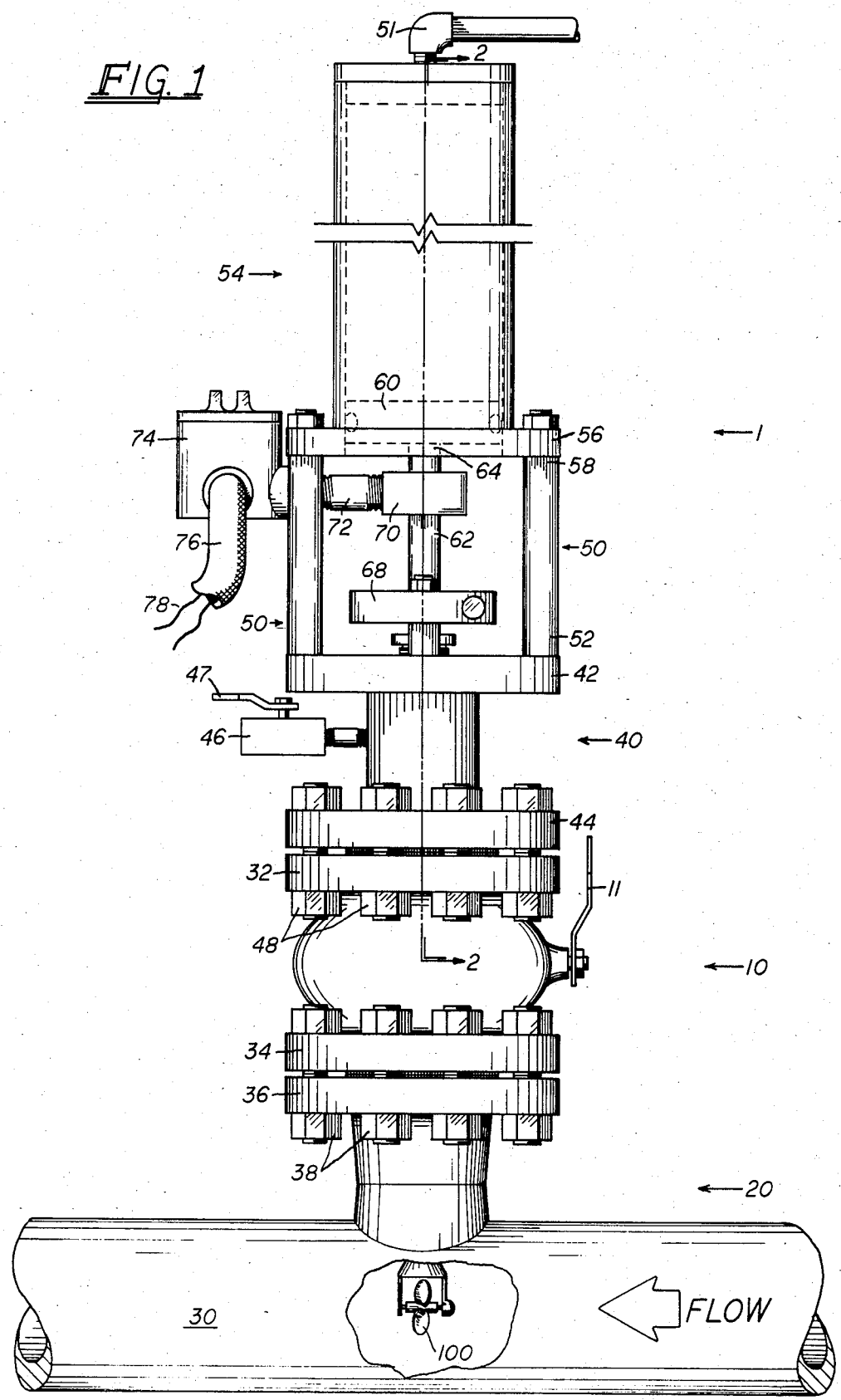
FIG. 1 is a perspective view of the automatic insertion device mounted on a valve which is mounted on a riser on a pressurized fluid pipeline. A turbine meter is shown fully inserted in the pipeline.

FIG. 1 is a perspective view of the preferred embodiment. In FIG. 1, the automatic insertion device is generally identified by the numeral 1 and is shown mounted on a valve generally identified by the numeral 10. The valve 10 is mounted on a riser or tee generally identified by the numeral 20. The riser is connected to and communicates with a pressurized fluid pipeline 30. The pipeline 30 is used for transporting natural gas, crude oil or any other fluid. The term fluid is used in its broadest sense to include any liquid or gas. The flow in FIG. 1 is from the right hand side of the page to the left hand side of the page as designated in the drawing by the large arrow.

The valve 10 is typically a ball valve, the construction of which is well known to those skilled in the art; however, the valve 10 could be a gate valve or any other type of valve generally used in the oil and gas industry which has an axial bore through the center thereof. The valve 10 is opened and closed by movement of handle 11. The valve 10 has a first flange 32 and a second flange 34 which are perforated by a plurality of holes, not shown in the drawing. The riser 20 has a flange 36 on the end thereof. The flange 36 is also perforated by a plurality of holes. A gasket, not shown in the drawings, is placed between flange 34 of valve 10 and flange 36 of the riser 20 establishing a seal between the valve 10 and the riser 20. The holes, not shown, are aligned and flange 34 and flange 36 are connected by a plurality of nuts and bolts 38, commonly referred to as a bolt circle.

A spool, generally identified by the numeral 40, mounts on top of the valve 10. The spool 40 is commonly known in the pipeline industry as a "lubricator", although it performs no lubricating function. The spool has a first flange 42 on one end and a second flange 44 on the other end. The spools and flanges are perforated by a longitudinal bore 102 better seen in FIG. 2.

A bleed valve 46 is mounted on the spool 40 and communicates with the longitudinal bore 102 of said spool. The bleed valve 46 is opened and closed by movement of handle 47. The bleed valve is normally in a closed position to prevent leakage of fluid from the pressurized pipeline. The purpose of the bleed valve 46 is to provide a means to vent pressure from the longitudinal bore 102 of the spool 40 prior to removal from the valve 10. The second flange 44 of the spool 40 is perforated by a plurality of holes, not shown in FIG. 1, which align with the plurality of holes in flange 32 of valve 10. A gasket, not shown in the drawings, is placed between second flange 44 of the spool 40 and the first flange 32 of the valve 10. The spool 40 is mounted on and connected to the valve 10 by a plurality of nuts and bolts 48, commonly known as a bolt circle.

A plurality of elongate spacers are generally identified by the numeral 50. The elongate spacers have a first end 52 which threads into the first flange 42 of the spool 40. An elongate cylinder is generally identified by the numeral 54. The elongate cylinder 54 has a flange 56 on one end thereof for detachably mounting the cylinder 54 on the second end 58 of spacer 50.

A piston 60 is shown in phantom inside of the cylinder 54. A piston rod 62 has a first end 64 which is removably connected to the piston 60, and a second end 66, better seen in FIG. 2. A lock collar 68 limits the depth of penetration of the second end 66 of the piston rod 62 and to the pressurized pipeline 30. A yoke 70 is mounted on the piston rod 62 and supports a pipe nipple 72. The pipe nipple supports a junction box 74. A flexible conduit 76 connects with the junction box 74.

Piping 51 is connected to the cylinder 54. The piping 51 communicates with the interior of the cylinder 54 and provides an inlet for pressurized fluids for operation of the piston 60, shown in phantom. When a pressurized fluid is injected through the piping 51 into the cylinder 54, the piston 60 moves causing insertion of the piston rod 62 through the spool 40, the valve 10 and the riser 20 into the pipeline 30. The forces exerted on the piston 60 to achive insertion of the piston rod 62 into the pipeline 30 must be sufficient to overcome the opposing forces acting on the second end 66 of the piston rod 62. The opposing forces are generated by the pressurized fluid inside of the pipeline 30 acting upon the second end 66 of the piston rod 62. To withdraw the piston rod 62 from the pipeline 30, the cylinder 54 must be vented through the pipeline 51. Venting allows the forces acting on the second end 66 of the piston rod 62 to overcome the forces acting on the piston 60, whereby the piston 60 moves back in the cylinder 54 and withdraws the second end 66 of the piston rod 62 from the pipeline 30. The second end 66 of the piston rod 62 comes to rest inside the longitudinal bore 120 of the spool 40 when the apparatus is in the fully withdrawn position as shown in FIG. 2.

In the preferred and illustrated embodiment, electrical wires 78 run through the flexible conduit 76, the junction box 74, the nippple 72, the yoke 70 and the piston rod 62 to the second end 66 thereof. The electrical wires typically connect to a proximity switch or other electrical sensor for measuring the velocity of the turbine 100 shown inserted in the pipeline 30. The turbine 100 is shown in diagrammatic format in FIG. 1. The exact configuration and operation of the turbine is well known to those skilled in the art. Many designs and different configurations of turbines are available from major manufacturers such as Daniel Industries, Inc., Electronic Flow-Meters, Inc., Flow Technology Incorporated, and ITT Barton Process Instruments and Controls. The volume of flow through the pipeline may be calculated given the rate of rotation of the turbine 100. This entire configuration will be referred to as a turbine meter. The term turbine meter as used in this disclosure includes the automatic insertion device, a turbine, a proximity switch or other sensor mounted in the second end of the piston rod, external instrumentation for measuring flow and wiring to connect the proximity switch to the external instrumentation.

Figure 2:
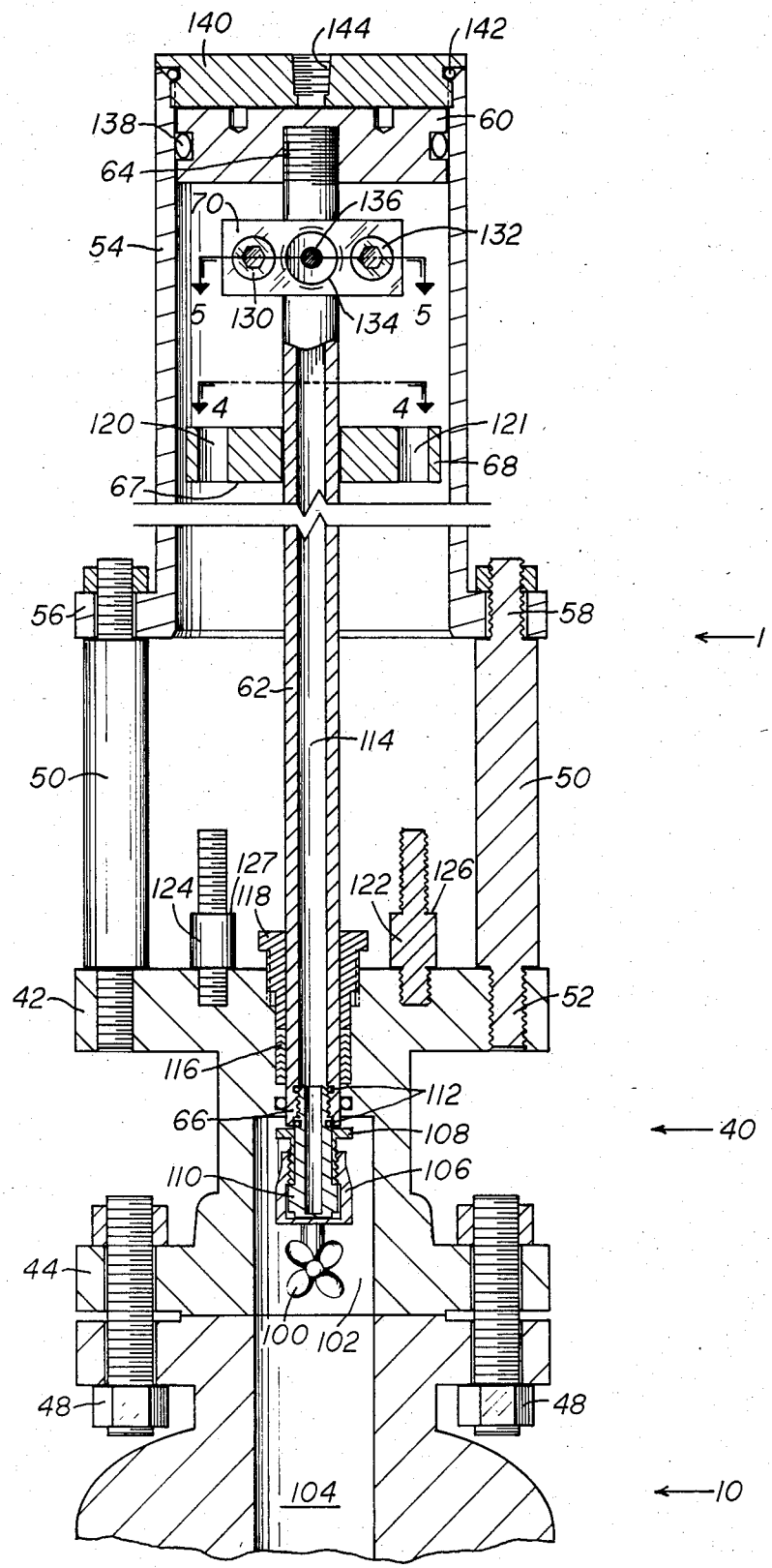
FIG. 2 is a section view of the automatic insertion device along the line 2—2 of FIG. 1 showing a turbine meter fully withdrawn from the pipeline.

FIG. 2 is a section view of the automatic insertion device 1 taken along the line 2—2 of FIG. 1. In FIG. 2, the turbine 100 has been withdrawn from the pipeline 30 into the longitudinal bore 102 of the spool 40. In this retracted position, fluid flow does not operate the turbine. Typically, the turbine is retracted to be serviced, or perhaps permit a pipeline pig to pass. The turbine, when inserted, is best returned to a centerline position to enable accurate flow measurements to be captured. The section view of the valve 10 shows a passageway 104 through which the turbine 100 is inserted when the valve 10 is in the open position. When the valve 10 is closed, the passageway 104 is blocked and isolated from the pressurized fluid in the pipeline 30. If the automatic insertion device is to be removed from the valve 10, the bleed valve 46, shown in FIG. 1, is opened to depressurize the longitudinal bore 102 before release of the bolt circle 48.

The turbine 100 is mounted on a shaft which connects to the turbine support 106. A threaded nut 108 engages the turbine support 106 to rigidly lock these elements to a cap 110 which is threaded into the second end 66 of the piston rod 62. The O-rings 112 or other suitable seal means are located between the cap 110 and the piston rod 62 to prevent pressurized flud from the pipeline 30 from entering the hollow axial passage 114 of the piston rod 62. A plurality of chevron packing 116 or other suitable seal means extend around the piston rod 62 and are located in the spool 40 to prevent leakage of fluid from the pressurized pipeline from the longitudinal bore 102 of the spool 40 to atmosphere. A packing gland 118 threadably engages the spool 40 to support and apply pressure to the plurality of chevron packing 116. If a slight leak develops, the packing gland 118 is tightened to apply more pressure to the chevron packing to seal the leak.

The second flange 44 of the spool 40 is connected to the valve 10 by the bolt circle 48. The first flange 42 of the spool 40 supports a plurality of elongate spacers 50. The spacers 50 are a one piece construction and are threaded on both ends. The first end 52 of the elongate spacer 50 threadably engages the first flange 42 of the spool 40. The second end 58 of the spacer 50 threadably engages and supports the flange 56 of the cylinder 54. Elongate spacers 50 separate the cylinder 54 from the spool 40 providing a work area with convenient access. For example, if the packing gland 118 needs to be tightened, sufficient open area is available for a workman to reach the packing gland 118 for tightening. The lock collar 68 is performed by hole 120 and 121 which are aligned to fit over a first post 122 and a second post 124. These posts have circular shoulders 126 and 127 to engage and support the lock collar 68 when the turbine 100 is inserted into the pressurized pipeline 30.

The yoke 70 has a first bolt 130 and a second bolt 132 therein. The bolts are better seen in section in FIG. 5. The yoke 70 has a threaded throat 134 which is aligned with a port 136 in the piston rod 62. The port 136 perforates the piston rod and allows communication between the exterior and the interior hollow axial passage 114.

The first end 64 of the piston rod 62 threadably engages the piston 60. An O-ring 138 or other suitable seal means is located between the piston 60 and the cylinder 54. A cylinder cap 140 threadably engages the cylinder 54 on the end opposite the flange 56. An O-ring 142 or other suitable seal means is located between the cylinder cap 140 and the cylinder 54 to prevent the escape of fluid from the cylinder 54. A port 144 is located in the cylinder cap 140 and is connected to suitable piping 51 as shown in FIG. 1. The port 144 functions as an inlet for fluid into the cylinder 54 for actuating the piston 60 for inserting the piston rod into pipeline 30. When the piston rod 62 is withdrawn from the pipeline, the port 144 functions as a vent or outlet to allow fluid to escape from the cylinder 54 as the piston 60 moves back toward the cylinder cap 140.

Figure 3:
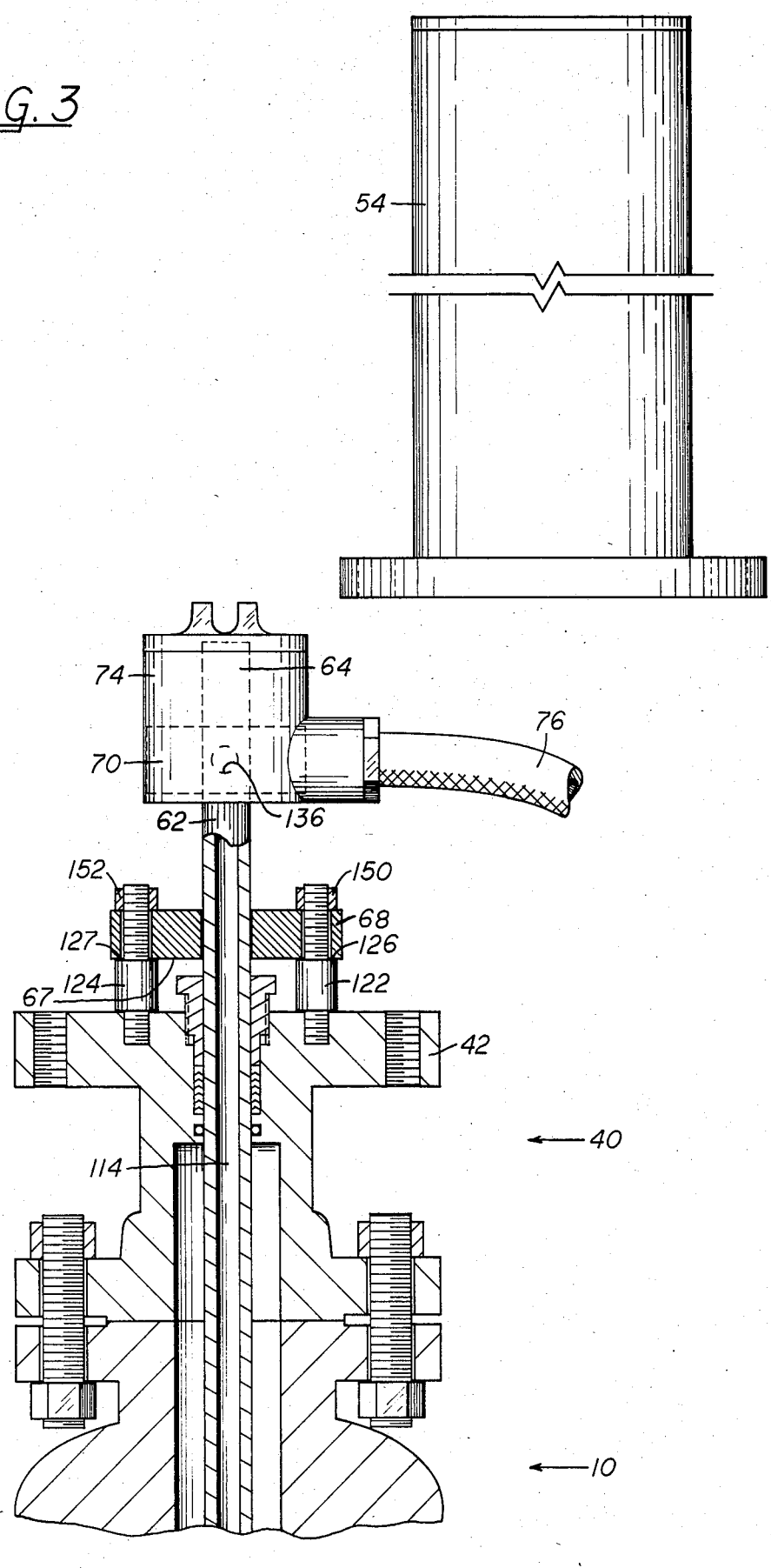
FIG. 3 is a partial section view of the automatic insertion device showing the cylinder removed from the spool.

In FIG. 3, the automatic insertion device is shown in a partial section view with the piston rod 62 fully inserted into the pipeline 30, not shown in this drawing. The cylinder 54 has been removed from the first flange 42 of the spool 40. The piston 60 has been removed from the piston rod 62 and is therefore not shown in FIG. 3. The lower surface 67 of the lock collar 68 engages and is supported by the shoulder 126 on first post 122 and the shoulder 127 on second post 124. A nut 150 threadably engages the first post 122 and a second nut 152 threadably engages the second post 124, thus securing the collar 68 on posts 122 and 124. Because the lock collar 68 firmly grips the piston rod 62, it limits the depth of penetration of the piston rod 62 into the pipeline 30. The junction box 74 and the flexible conduit 76 are shown in perspective. The yoke 70 is shown in phantom attached to the first end 64, also shown in phantom, of the piston rod 62. The port 136 is also shown in phantom which allows communication between the hollow axial passage 114 in the piston rod 62, and the junction box 74 and the flexible conduit 76.

Figure 4:
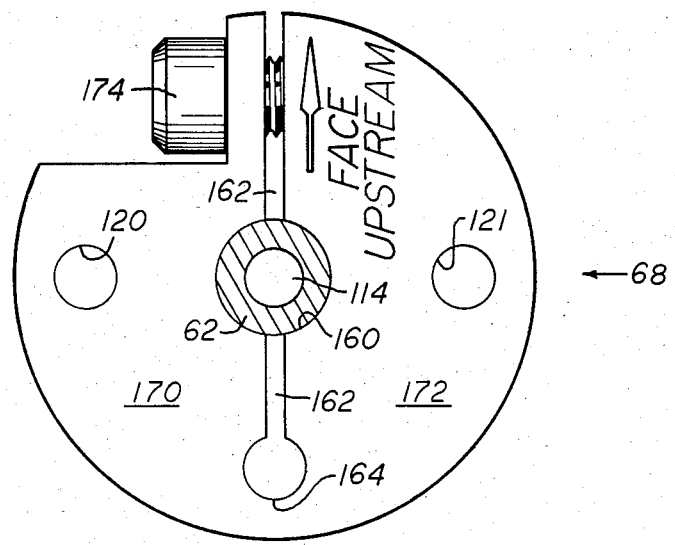
FIG. 4 is a plan view of the lock collar taken along lines 4—4 of FIG. 2.

In FIG. 4, the lock collar 68 is shown along the line 4—4 in FIG. 2. The lock collar 68 has a center hole 160 which is sized to receive the piston rod 62 which is shown in section view in this figure. The hollow axial passage 114 is shown in the center of the piston rod 62. The holes 120 and 121 are shown passing all the way through the lock collar 68. The lock collar has a radial slot 162 which passes along the diameter of the collar 68 through the center hole 160 to a stopping point 164 which is recessed away from the circumference of the disc-shaped collar 68. The slot 162 divides the collar 68 into two clam-shaped sections 170 and 172. A threaded bolt 174 extends through a hole in the clam-shaped section 170 and is received by a threaded hole, not shown in this drawing, in the other clam-shaped section 172. When the bolt 174 is tightened, it causes section 170 to be drawn towards section 172 which results in a very tight mechanical grip on the piston rod 62. When the bolt 174 is fully tightened, it causes the collar 68 to be mechanically locked to the piston rod 62. When the collar 68 is locked to the rod 62, they move as one integral part.

Figure 5:
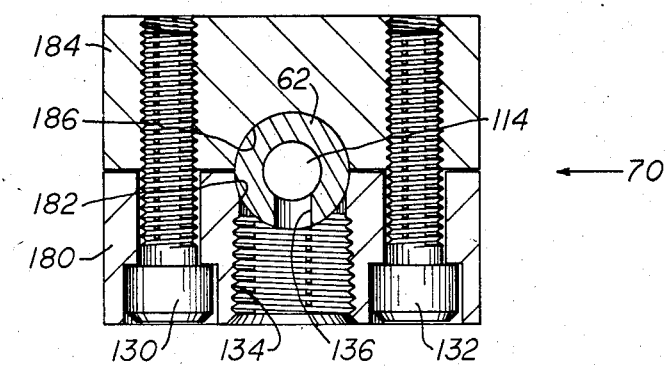
FIG. 5 is a section view of the yoke taken along lines 5—5 of FIG. 2.

In FIG. 5, the yoke 70 is shown in section view along the line 5—5 of FIG. 2. The yoke is divided into a first rectangular section 180 with a semi-circular bore 182 through the edge thereof and a second rectangular section 184 with a semicircular bore 186 through the edge thereof. The semicircular bores are sized to receive and grip the piston rod 62 as shown in section view. The port 136 which perforates the piston rod 62 is clearly shown allowing communication with the hollow axial passage 114 in the piston rod. A threaded throat 134 passes through the first rectangular section 180 of the yoke 70 and communicates with the hollow axial passage 114 through the port 136. A first bolt 130 and a second bolt 132 pass through the first rectangular section 180 of the yoke 70 and threadably engage the second rectangular section 184 of the yoke 70. When the bolts 130 and 132 are tightened, first rectangular section 180 and the second rectangular section 184 mechanically grip the piston rod 62, securely locking the yoke 70 about the piston rod 62. The threaded throat 134 provides a secure point of mounting for a pipe nipple 72, better seen in FIG. 1. The junction box 74 mounts on the pipe nipple 72 as shown in perspective in FIG. 1.

Operation of the Preferred Embodiment

In a typical situation, a pipeline will be in place transporting various fluids. An engineering decision will be made to place a turbine meter or other sensor at a specific position in the pipeline in order to measure flow. In order to accomplish this task, a "hot tap" will be made into the pipeline, and a riser 20 will be welded onto the pipeline 30. The installation of a hot tap in an operational pipeline is well known to those skilled in the art. The term turbine meter includes the automatic insertion device, a turbine, a proximity switch mounted in the piston rod, external instrumentation for measuring flow and wiring to connect the proximity switch to the external instrumentation.

In some situations, a tee may be preexisting in the pipeline and will serve the same purpose as a riser 20. Both the tee and the riser provide an access point to the pipeline and provide a flange for mounting of other devices. For purposes of this disclosure, the word tee and riser are synonymous.

A valve will be connected to the flange of the riser, thus preventing the escape of pressurized fluid from the pipeline. The valve will typically be of a ball-type construction which has an axial bore through the middle thereof, allowing insertion of the turbine. Other types of valves are satisfactory for this application so long as they have an axial bore which will permit passage of the piston rod and turbine or other sensors to be described hereinafter.

Prior to installation of the turbine, the operator must determine two important factors, i.e. the depth of penetration of the turbine into the pipeline and the azimuthal orientation of the turbine relative to the flow in the pipeline.

(a) Depth of Penetration—Prior to installation of the automatic insertion device, it will be necessary to calculate the amount of travel of the piston rod. The collar will thereafter be locked on the piston rod at the appropriate depth. For example, in a 24 inch pipeline, the turbine meter will typically to positioned on the center line of the pipeline which will require 12 inches of travel. The 2 inch diameter standard riser will require approximately 11 inches of travel. A standard valve suitable for this installation is typically 11½ inches in length from flange face to flange face. The piston rod will therefore need to travel 34½ inches from the fully retracted position to the fully inserted position so that the turbine will be positioned in the center of the pipeline. The 34½ inches of travel is the sum of; 12 inches required to center the turbine in the pipe, 11 inches for the riser, and 11½ inches for the valve. Prior to installing the collar 68, the piston rod 62 must be fully retracted into the cylinder 54. The lower surface 67 of the collar 68 will then be locked on the piston rod exactly 34½ inches from the circular shoulders 126 and 127 on the mounting posts. After the collar is securely locked to the piston rod, the amount of possible travel or penetration into the pipeline will be fixed. This precisely positions the turbine or other sensor in the pipeline and also prevents the possibility of the piston rod being thrust through the pipeline.

(b) Azimuthal Orientation—In order for turbine meters, vortex shedding meters, pitot probes, doppler measuring devices, and samplers to properly operate, they must be correctly oriented in relation to the direction of flow of fluid in the pipeline. In a typical turbine, the blades must be oriented normal to the flow of fluid in the pipeline. In order to achieve this precise azimuthal orientation, the lock collar has an arrow stamped on the top thereof and the phrase "face upstream" stenciled next to the arrow. Prior to tightening of the the collar, the piston rod is rotated so that the blades in the turbine are correctly oriented with the arrow on the top of the lock collar. This orientation should be accomplished prior to installation of the automatic insertion device. When the lock collar is correctly positioned on the first and second posts, the angle of orientation will be correct relative to the flow in the pipeline.

After the lock collar has been properly installed on the piston rod for both azimuthal orientation and depth of penetration, the automatic insertion device can be mounted on the first flange of the valve with a bolt circle. After the bolt circle has been properly tightened, the valve will be opened which will allow pressurized fluid in the pipeline to move into the longitudinal bore in the spool. The chevron packing surrounding the piston rod and the O-rings between the cap and the piston rod prevent the escape of pressurized fluid from the pipeline.

To insert the piston rod into the pipeline, a fluid will then be injected under pressure through the piping and port in the cylinder cap causing movement of the piston towards the spool. As the piston slidably moves down the cylinder, the second end of the piston rod will move through the spool, past the the valve and the riser into the pressurized pipeline. Any suitable pressurized fluid source may be used for actuation of the piston, e.g. pressurized nitrogen, hydraulic fluid, natural gas or product from the pipeline itself.

In most applications, after the turbine or other sensor has been inserted into the pipeline, the nuts will then be tightened on the first and second post, thus securing the lock collar to the lubricator spool. The arrow indicating the azimuthal orientation of the piston rod must be correctly oriented. The cylinder and spacers will then be removed from the spool. The piston will then be unscrewed from the first end of the piston rod.

In most applications, the proximity switch or other electronic sensor will be installed in the cap prior to insertion in the pipeline. Wires will pass through the hollow axial passage of the piston rod through the port and hang out of the threaded throat of the yoke. After removal of the cylinder, the pipe nipple and junction box will be installed. The wires coming from the sensor will then be connected in the junction box with wires coming from remote instrumentation through the flexible conduit.

Removal of the cylinder prevents an accidental withdrawal of the turbine which could result in serious dollar loss if flow was not measured for a period of days or weeks. In addition, removal of the cylinder allows the pipeline operator to reduce his operating costs because only one cylinder is needed to operate a multitude of turbines or other sensors.

The present invention is approximately 40% shorter than prior art devices when measured before insertion of the turbine or other sensor into the pipeline. After insertion of the turbine or other sensor into the pipeline, the cylinder can be removed, which further reduces the overall length of the apparatus.

This reduction in overall length is of particular advantage in aboveground parallel piping situations which require a horizontal insertion device. This reduction in length is also advantageous in other aboveground applications when the insertion device must be positioned either horizontally or vertically inside of a small metal building. Any reduction in overall length will minimize the size of a pit if a horizontal insertion device is required. It should be noted that other prior art devices have removable cylinders. Thus, the primary advantage of the present invention is the 40% reduction in overall length of the device prior to insertion in the pipeline and prior to removal of the cylinder.

Figure 6:
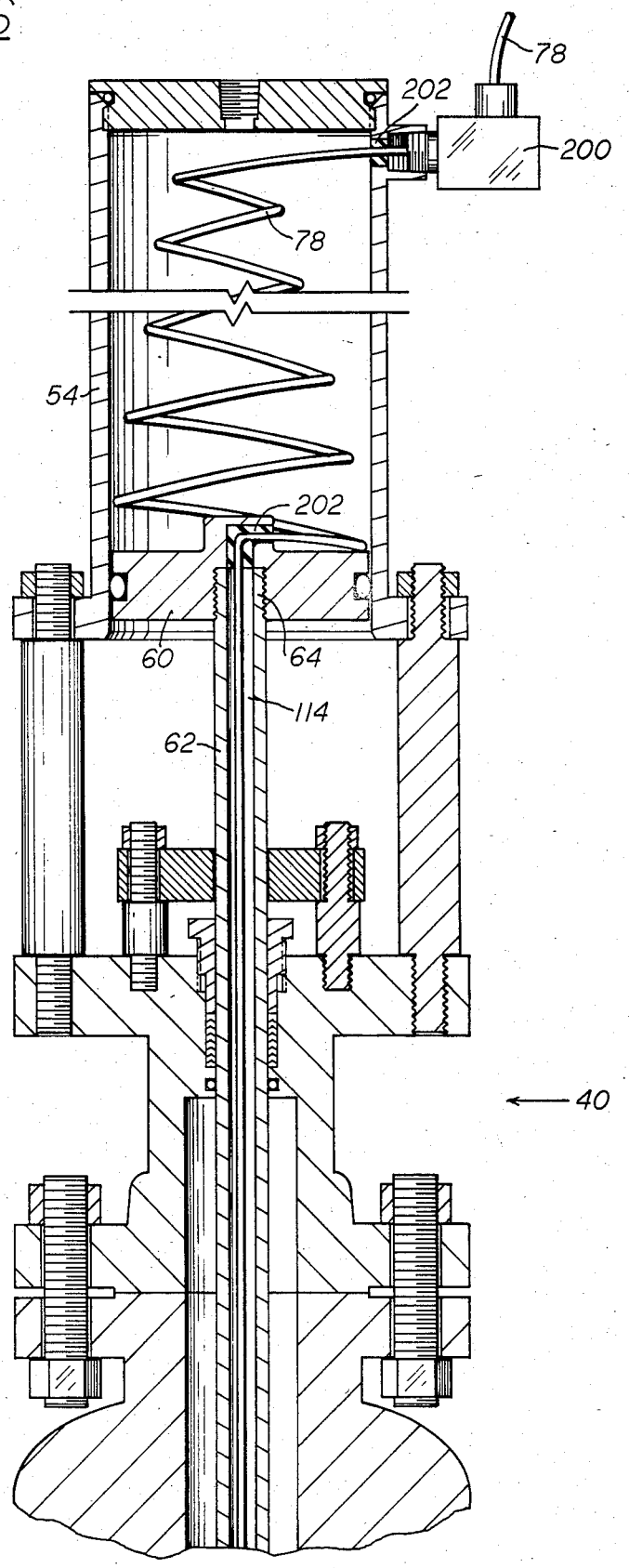
FIG. 6 is a section view of an alternate embodiment of the automatic insertion device with a nonremovable cylinder.

In FIG. 6, an alternate embodiment is shown wherein the cylinder 54 is not designed to be removed from the spool 40. This alternative embodiment is shown with the piston rod 62 and the piston 60 in a fully inserted position. The parts and operation of this alternative embodiment are identical to the parts and operation of the preferred embodiment as described in FIGS. 1–5 with several exceptions.

The alternate embodiment shown in FIG. 6 does not use the yoke 70 shown in FIG. 5, the pipe nipple 72 shown in FIG. 1, or the junction box 74 shown in FIGS. 1 and 3. Instead, the wire 78 runs directly from the axial hollow passage 114 through the first end 64 of the piston rod 62 and through the piston 60. The wire 78 then passes through the interior of the cylinder 54 and out a fitting 200. The wire is sealed where if enters and leaves the cylinder 54 by appropriate elastomeric seal means 202. This seal means 202 prevents the escape of fluid from the cylinder 54 during operation. Because the wire 78 passes through the cylinder 54, the cylinder is not designed to be removed from the spool 40. Although the embodiment shown in FIG. 6 does not have a removable cylinder, it still achieves the 40% overall reduction in length when compared with prior art insertion devices. Again, this reduction in overall length is calculated prior to insertion of the piston rod into the pipeline and prior to removal of the cylinder.

FIG. 7 is a section view of another embodiment which is suitable for use as a pressure sensor or to remove liquids from the pipeline. The primary components and operation of this alternate embodiment are identical to the primary components and operation of the preferred embodiment shown in FIGS. 1–5 with the following exceptions: there is no yoke 70, pipe nipple 72, junction box 74, turbine 100, turbine support 106, cap 108 or seal means 112.

The second end 66 of the piston rod 62 is open to allow communication between the pressurized fluid in the pipeline and the hollow axial interior 114 of the piston rod 62. The first end 64 of the piston rod 62 is also open allowing communication with the hollow axial passage 114. The first end 64 of the piston rod 62 threadably engages the piston 60 and a short portion 210 extends beyond the piston 60. The short portion 210 threadably engages a mount 212 which has a port 214 which communicates with the hollow axial passage 114 and the pressurized fluid in the pipeline 30. A valve 216 threadably engages the port 214 in the mount 212. During installation of this automatic insertion device, a plug 218 is inserted in the mouth of the valve, thereby isolating the valve from the pressurized fluid used for actuation of the piston 60. During installation, the valve 216 would be in the closed position. A circular ring 220 is mounted between the piston 60 and the cylinder cap 140. The ring 220 acts as a spacer or stop to prevent the piston 60 from being withdrawn such that the valve 216 would jam against the cylinder cap 140. The alternative embodiment shown in FIG. 7 would be installed on the pipeline in the same fashion as described for the preferred embodiment; however, azimuthal orientation is not critical for sensing temperature or pressure or for removing liquids from the pipeline. Azimuthal orientation is critical for turbine meters, vortex shedding meters, pitot probes, doppler measuring devices, and samplers.

After the piston rod 62 has been inserted to the desired depth in the pipeline, the cylinder 54 and the spacers 50 would be removed. The piston 60 would remain in place in this embodiment. The plug 218 would be removed and suitable piping, not shown, to remote instrumentation would be installed. After installation of such suitable piping, the valve 216 would be opened allowing the instrumentation to sense the pressure or to remove fluid directly from the pipeline 30.

FIG. 8 shows an alternate embodiment of a cylinder 230 which has a flange 232 on one end thereof for direct connection to the first flange 42 of the spool 40. The cylinder 230 has a window 234 in the side thereof.

FIG. 9 is a section view of the alternate embodiment which uses the window 234 shown in FIG. 8. The window 234 is shown in phantom. The cylinder 230 operates in the same fashion as the cylinder 54 in the preferred embodiment shown in FIGS. 1-5, except that the plurality of spacers 50 have been eliminated. In this alternate embodiment, the flange 232 directly connects to the first flange 42 of the spool 40 by a plurality of bolts 236. In this alternate embodiment, access to the lock collar 68 and first and second posts 122 and 124 is through window 234. After the lock collar 68 has been secured to the first post 122 and the second post 124, the cylinder 230 can be removed from the spool 40. The same advantages pertain to the embodiment shown in FIGS. 8 and 9 regarding the reduction in height that were previously discussed for the preferred embodiment in FIGS. 1-5.

FIG. 10 is a section view of an alternative embodiment of the automatic insertion device integrated with a pump or sampler. For purposes of this disclosure, the terms pump and sampler are synonymous. The apparatus is shown in a fully withdrawn position with the pump 250 nestled in the spool 40. The installation and insertion of the sampler in the alternative embodiment shown in FIG. 10 is similar to the installation and insertion of the turbine shown in the preferred embodiment in FIGS. 1-5.

The numeral 250 generally refers to a means for pumping an aliquot portion of pressurized fluid from the pressurized pipeline 30. In this alternate embodiment, a master piston 252 is slidably mounted in the cylinder 54. An O-ring 300, or other suitable seal means, is located between the master piston 252 and the cylinder 54. Attached to the undersigned of the master piston 252 is a coupling 254 which threadably engages a neck 256 which is a part of and extends out of the master piston 252. An outer shaft 258 threadably engages with the coupling 254. The outer shaft 258 therefore moves in tandem with the master piston 252. Upon reciprocation of the master piston 252, the outer shaft 258 is either inserted or withdrawn into the pipeline 30.

The pumping means consists of the following elements: an elongate piston rod 260 with a first end 262, a second end 264, and a hollow axial interior 265. The piston rod 260 is threadably engaged with a piston 266. The piston 266 is slidably mounted inside of the master piston 252. An O-ring 302, or other suitable seal means, is located between the piston 266 and the interior of the master piston 252. The piston 266 divides the interior of the master piston 252 into a first chamber 267 and a second chamber 269. The piston rod 260 is reciprocated upon movement of the piston 266.

A first port 251 in the master piston 252 allows communication with first chamber 267; a second port 253 in master piston 252 allows communication with second chamber 269. The first port 251 is blocked by a plug 255 during installation; likewise, the second port 253 is blocked by a plug 257. A third plug 259 is threaded in the first end 262 of piston rod 260 during installation. A slip ring 261 prevents the master piston 252 from being withdrawn too far in the cylinder 54 and bumping the plug 259 into cylinder cap 140.

A check valve means 268 is located in the second end 264 of the piston 260. A body 270 is mounted on the second end of the outer shaft 258. This body has a passageway 276 which allows fluid to enter and exit the body when it is inserted inside of the pressurized fluid pipeline 30. A resilient member 278 is located in the body and has a dimple-shaped cavity 280 therein which is exposed to the passageway 276. The resilient member 278 is confined by a hollow sleeve 282 which is mounted in the body 270.

A plurality of Chevron packing 263 or other seal means encircles the outer shaft 258 in spool 40 preventing the escape of pressurized fluid from the pipeline 30. A plurality of chevron packing 265 or other suitable seal means encircles the piston rod 260 in connector 254 preventing escape of pressurized fluid from the pipeline 30.

Operation of the Alternate Embodiment Shown in FIG. 10

Prior to installation of the alternate embodiment shown in FIG. 10 which is used for pumping or sampling an aliquot portion of the pressurized fluid in the pipeline, the lock collar 68 must be positioned on the outer shaft 258 in the same fashion as described for the preferred embodiment. After the lock collar has been positioned, the pump will be inserted into the pipeline. The spacers and the cylinder will then be removed from the spool.

The plugs in the master cylinder will then be removed and suitable piping will be attached for periodic actuation of the piston 266. In addition, the plug in the first end of the piston rod 260 will be removed. A sample container will be connected with suitable piping to the first end of the piston rod to transfer and store an aliquot portion of the pressurized fluid removed from the pipeline by this pumping device. In order to take a sample or pump an aliquot portion of fluid from the pipeline through the piston rod 260, pressurized fluid must be applied through the port 251 into the first chamber 267 causing the piston 266 to reciprocate in the master piston 252. The second end of the piston rod 264 moves through the passageway 276 and comes into contact with the resilient member 278. An aliquot of pressurized fluid is trapped in the cavity 280. As greater pressure is applied to the piston 266, the resilient member will be collapsed and the aliquot portion of sample will move past the check valve means 268 into the hollow axial passage 265 of the piston rod 260. The aliquot portion of pressurized fluid withdrawn from the pipeline is commonly referred to as a sample. The sample would then be transferred via appropriate piping to a vessel or other sample container, not shown in the drawings.

The pressure in the first chamber 267 is then relieved and opposing pressure is applied via port 253 into the second chamber 269 causing the piston 266 to move in the opposite direction. This reverse movement separates the second end 264 of the piston rod 260 from the resilient member 278. The piston rod 260 thus returns to its original position ready to take another sample. This completes one down and up stroke of the sampler. This stroking or pumping action is typically repeated periodically in order to collect a representative sample of fluid from the pipeline.

While the foregoing is directed to the preferred embodiment of the present invention, other and further embodiments of the invention may be devised without departing from the basic scope thereof, and the scope thereof is determined by the claims which follow.

What is claimed is:

1. An apparatus to insert and remove a piston rod into and from a pressurized fluid pipeline through a valve mounted on a tee connected to the pressurized pipeline comprising:
   (a) a spool having a first flange on one end and a second flange on the other end, said second flange being connected to said valve, said spool and said flanges being perforated by a longitudinal bore;
   (b) an elongate cylinder having a flange on one end for detachable mounting of said cylinder;
   (c) a plurality of elongate spacers with a first end releasably connected to said first flange of said spool and a second end releasably connected to said flange of said cylinder, said spacers positioning said cylinder in axial alignment with said longitudinal bore of said spool;
   (d) a piston slidably mounted in said cylinder;
   (e) said piston rod having a hollow axial passage, a first end removably connected to said piston, a second open end allowing access to said hollow passage and a port perforating said piston rod and communicating with said hollow passage, said piston rod extending through said longitudinal bore of said spool and said second end of said piston rod positioned for insertion and removal through said valve and said tee into and from said pressurized pipeline on reciprocation by said piston;
   (f) means for limiting the depth of penetration of said second end of said piston rod into said pressurized pipeline including:
      (i) a disk-shaped collar having a center hole to receive said piston rod;
      (ii) said collar having a radial slot along the diameter thereof and through said center hole which divides said collar into two clam-shaped sections;
      (iii) a threaded bolt passing through one of said clam-shaped sections into a threaded hole in the other of said clam-shaped sections, said bolt causing said clam-shaped sections to grip said piston rod when tightened and locking said collar to said piston rod; and
      (iv) a first post and a second post mounted on said first flange of said spool on opposite sides of said longitudinal bore, said posts having circular shoulders to engage and support said collar which, when locked to said piston rod, limits the depth of penetration of said second end of said piston rod into said pressurized pipeline;
   (g) seal means extending around said piston rod to prevent leakage of said fluid from said pressurized pipeline.

2. The apparatus of claim 1 further including a valve connected to said port in said piston rod to control the passage of fluids from said pressurized pipeline through said second open end and said hollow passage of said piston rod.

3. The apparatus of claim 1 further including:
   (a) a cap connected to said second open end of said piston rod;
   (b) means for sensing the temperature of said fluid in said pressurized pipeline and for converting temperature into an output signal, said sensing means attached to said cap;
   (c) means for transmitting said output signal from said sensing means through said hollow passage and said port of said piston rod; and
   (d) seal means located between said cap and said piston rod to prevent leakage of said fluid from said pressurized pipeline.

4. The apparatus of claim 1 further including means for orienting said piston rod to a predetermined azimuthal orientation relative to the flow through said pipeline.

5. The apparatus of claim 4 wherein said collar further includes: a hole through one of said clam-shaped sections and another hole through the other of said clam-shaped sections, said holes sized to receive said posts which orient said collar to a predetermined azimuthal orientation relative to the flow through said pipeline.

6. The apparatus of claim 5 further including a pitot probe connected to said second end of said piston rod.

7. The apparatus of claim 4 further including:
   (a) a cap connected to said second open end of said piston rod; and
   (b) seal means located between said cap and said piston rod to prevent leakage of fluid from said pressurized pipeline.

8. The apparatus of claim 7 further including:
   (a) a turbine mounted on and extending from said cap;
   (b) means for sensing the speed of said turbine and converting speed into an output signal; and
   (c) means for transmitting said output signal from said sensing means through said hollow passage and said port of said piston rod.

9. The apparatus of claim 8 including:
   (a) a yoke supporting a pipe nipple and a junction box;
   (b) wherein said yoke has a first rectangular section with a semicircular bore through the edge thereof and a second rectangular section with a semicircular bore through the edge thereof, said semicircular bores sized to receive and grip said piston rod;
   (c) first and second bolts connecting said first and said second sections of said yoke about said piston rod; and
   (d) a threaded throat through said first rectangular section of said yoke which communicates with said hollow passage of said piston rod through said port, said threaded throat receiving and supporting said pipe nipple and said junction box.

10. The apparatus of claim 9 wherein the limiting means includes:
    (a) a disk-shaped collar having a center hole to receive said piston rod;
    (b) said collar having a radial slot along the diameter thereof and through said center hole which divides said collar into two clam-shaped sections;

(c) a threaded bolt passing through one of said clam-shaped sections into a threaded hole in the other of said clam-shaped sections, said screw causing said clam-shaped sections to grip said piston rod when tightened and locking said collar to said piston rod; and (d) a first post and a second post mounted on said first flange of said spool on opposite sides of said longitudinal bore, said posts having circular shoulders to engage and support said collar which, when locked to said piston rod, limits the depth of penetration of said second end of said piston rod into said pressurized pipeline.

11. The apparatus of claim 9 further including:

(a) a cap connected to said second open end of said piston rod;

(b) means for sensing the temperature of a fluid in said pressurized pipeline and for converting said temperature into an output signal, said sensing means attached to said cap;

(c) means for transmitting said output signal from said sensing means through said hollow interior and said port of said piston rod; and (d) seal means located between said cap and said piston rod to prevent leakage of said fluid from said pressurized pipeline.

12. The apparatus of claim 4 further including:

(a) first means for sending sound waves through said fluid in said pressurized pipeline; and (b) second means receiving sound waves through said fluid in said pressurized pipeline, said second means located 180° opposite said first means in said pressurized pipeline.

13. The apparatus of claim 5 wherein the limiting means includes:

(a) a disk-shaped collar having a center hole to receive said piston rod;

(b) said collar having a radial slot along the diameter thereof and through said center hole which divides said collar into two clam-shaped sections;

(c) said clam-shaped sections into a threaded hole in the other of said clam-shaped sections, said screw causing said clam-shaped sections to grip said piston rod when tightened and locking said collar to said piston rod; and (d) a first post and a second post mounted on said first flange of said spool on opposite sides of said longitudinal bore, said posts having circular shoulders to engage and support said collar which, when locked to said piston rod, limits the depth of penetration of said second end of said piston rod into said pressurized pipeline.

14. An apparatus to insert and remove a piston rod into and from a pressurized fluid pipeline through a valve mounted on a tee connected to the pressurized pipeline comprising:

(a) a spool having a first flange on one end and a second flange on the other end, said second flange being connected to said valve, said spool and said flanges being perforated by a longitudinal bore;

(b) an elongate cylinder with circular walls having a window in a portion of said circular wall and having a flange on one end of said cylinder to detachably mount said cylinder on said first flange of said spool;

(c) a piston slidably mounted in said cylinder;

(d) said piston rod having a hollow axial passage, a first end removably connected to said piston, a second open end allowing access to said hollow passage and a port perforating said piston rod and communicating with said hollow passage, said piston rod extending through said longitudinal bore of said spool and said second end of said piston rod positioned for insertion and removal through said valve and said tee into and from said pressurized pipeline on reciprocation by said piston;

(e) means for limiting the depth of penetration of said second end of said piston rod into said pressurized pipeline; and (f) seal means extending around said piston rod to prevent leakage of fluid from said pressurized pipeline.

15. The apparatus of claim 14 further including a valve connected to said port of said piston rod to selectively control the passage of fluids from said pressurized pipeline, through said second open end and said hollow passage of said piston rod.

16. The apparatus of claim 14 further including means for orienting said piston rod to a predetermined azimuthal orientation relative to the flow through said pipeline.

17. The apparatus of claim 16 wherein the limiting means and orienting means includes:

(a) a disk-shaped collar having a center hole to receive said piston rod;

(b) said collar having a radial slot along the diameter thereof and through said center hole which divides said collar into two clam-shaped sections;

(c) a threaded bolt passing through one of said clam-shaped sections into a threaded hole in the other of said clam-shaped sections, said bolt causing said clam-shaped sections to grip said piston rod when tightened and locking said collar to said piston rod;

(d) a first post and a second post permanently mounted on said first flange of said spool on opposite sides of said longitudinal bore, said posts having circular shoulders to engage and support said collar which, when locked to said piston rod, limits the depth of penetration of said second end of said piston rod into said pressurized pipeline; and (e) said collar having one hole through one of said clam-shaped sections and another hole through the other of said clam-shaped sections, said holes sized to receive said posts which orient said collar to a predetermined azimuthal orientation relative to the flow through said pipeline.

18. The apparatus of claim 17 further including a pitot probe connected to said second end of said piston rod.

19. The apparatus of claim 16 further including:

(a) a cap connected to said second open end of said piston rod; and (b) seal means located between said cap and said piston rod to prevent leakage of fluid from said pressurized pipeline.

20. The apparatus of claim 19 further including:

(a) a turbine mounted on and extending from said cap;

(b) means for sensing the speed of said turbine and converting said speed into an output signal; and (c) means for transmitting said output signal from said sensing means through said hollow passage and said port of said piston rod.

21. The apparatus of claim 20 including:

(a) a yoke supporting a pipe nipple and a junction box;

(b) wherein said yoke has a first rectangular section with a semicircular bore through the edge thereof and a second rectangular section with a semicircular bore through the edge thereof, said semicircular bores sized to receive and grip said piston rod;

(c) first and second bolts connecting said first and said second sections of said yoke about said piston rod; and (d) a threaded throat through said first rectangular section of said yoke which communicates with said hollow interior of said piston rod through said port, said threaded throat receiving and supporting said pipe nipple and said junction box.

22. The apparatus of claim 16 further including:
(a) first means for sending sound waves through a fluid in said pressurized pipeline; and
(b) second means receiving sound waves through said fluid in said pressurized pipeline, said second means located 180° opposite said first means in said pressurized pipeline.

23. An apparatus to insert and remove a piston rod into and from a pressurized pipeline through a valve mounted on a tee connected to the pressurized pipeline comprising:
(a) a spool having a first flange on one end and a second flange on the other end, said second flange being connected to said valve, said spool and said flanges being perforated by a longitudinal bore;
(b) an elongate fluid actuated cylinder with circular walls having a window in a portion of said circular wall and having a flange on one end of said cylinder to mount said cylinder on said first flange of said spool;
(c) a piston slidably mounted in said cylinder;
(d) said piston rod having a hollow axial passage, a first open end communicating with said hollow passage, a second open end communicating with said hollow passage, said piston rod extending through said longitudinal bore of said spool and said second end of said piston rod positioned for insertion and removal through said valve and said tee into and from said pressurized pipeline on reciprocation by said piston;
(e) means for limiting the depth of penetration of said second end of said piston rod into said pressurized pipeline; and
(f) seal means extending around said piston rod to prevent leakage of fluid from said pressurized pipeline and seal means to prevent leakage of fluid from said cylinder.

24. The apparatus of claim 23 further including means for orienting said piston rod to a predetermined azimuthal orientation relative to the flow of said fluid through said pipeline.

25. An apparatus to insert and remove a piston rod into and from a pressurized fluid pipeline through a valve mounted on a tee connected to the pressurized pipeline comprising:
(a) a spool having a first flange on one end and a second flange on the other end, said second flange being connected to said valve, said spool and said flanges being perforated by a longitudinal bore;
(b) an elongate cylinder having a flange on one end for detachable mounting of said cylinder;
(c) a plurality of elongate spacers with a first end releasably connected to said first flange of said spool and a second end releasably connected to said flange of said cylinder, said spacers positioning said cylinder in axial alignment with said longitudinal bore of said spool;
(d) a piston slidably mounted in said cylinder;
(e) said piston rod having a hollow axial passage, a first end removably connected to said piston, a second open end allowing access to said hollow passage and a port perforating said piston rod and communicating with said hollow passage, said piston rod extending through said longitudinal bore of said spool and said second end of said piston rod positioned for insertion and removal through said valve and said tee into and from said pressurized pipeline on reciprocation by said piston;
(f) an axially adjustable lock collar gripping the external circumference of said piston rod;
(g) a stop abutting said lock collar and limiting the depth of penetration of said second end of said piston rod into said pressurized pipeline;
(h) means for securing said lock collar to said stop; and
(i) seal means extending around said piston rod to prevent leakage of said fluid from said pressurized pipeline.

26. The apparatus of claim 25 further including a valve connected to said port in said piston rod to control the passage of fluids from said pressurized pipeline through said second open end and said hollow passage of said piston rod.

27. The apparatus of claim 25 further including:
(a) a cap connected to said second open end of said piston rod;
(b) means for sensing the temperature of said fluid in said pressurized pipeline and for converting temperature into an output signal, said sensing means attached to said cap;
(c) means for transmitting said output signal from said sensing means through said hollow passage and said port of said piston rod; and
(d) seal means located between said cap and said piston rod to prevent leakage of said fluid from said pressurized pipeline.

28. The apparatus of claim 25 further including a pitot probe connected to said second end of said piston rod.

29. The apparatus of claim 25 further including:
(a) a cap connected to said second open end of said piston rod; and
(b) seal means located between said cap and said piston rod to prevent leakage of fluid from said pressurized pipeline.

30. The apparatus of claim 25 further including:
(a) a turbine mounted on and extending from said cap;
(b) means for sensing the speed of said turbine and converting speed into an output signal; and
(c) means for transmitting said output signal from said sensing means through said hollow passage and said port of said piston rod.

31. The apparatus of claim 30 including:
(a) a yoke supporting a pipe nipple and a junction box;
(b) wherein said yoke has a first rectangular section with a semicircular bore through the edge thereof and a second rectangular section with a semicircular bore through the edge thereof, said semicircular bores sized to receive and grip said piston rod;
(c) first and second bolts connecting said first and said second sections of said yoke about said piston rod; and
(d) a threaded throat through said first rectangular section of said yoke which communicates with said hollow passage of said piston rod through said port, said threaded throat receiving and supporting said pipe nipple and said junction box.

32. The apparatus of claim 25 further including:
(a) first means for sending sound waves through said fluid in said pressurized pipeline; and
(b) second means receiving sound waves through said fluid in said pressurized pipeline, said second means located 180° opposite said first means in said pressurized pipeline.

* * * * *